(12) United States Patent
Kramer et al.

(10) Patent No.: US 9,765,177 B2
(45) Date of Patent: *Sep. 19, 2017

(54) POLYMER CONTAINING SILANE GROUPS

(71) Applicant: SIKA TECHNOLOGY AG, Baar (CH)

(72) Inventors: Andreas Kramer, Zürich (CH); Urs Burckhardt, Zürich (CH)

(73) Assignee: SIKA TECHNOLOGY AG, Baar (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/398,584

(22) PCT Filed: May 22, 2013

(86) PCT No.: PCT/EP2013/060553

§ 371 (c)(1),
(2) Date: Nov. 3, 2014

(87) PCT Pub. No.: WO2013/174891

PCT Pub. Date: Nov. 28, 2013

(65) Prior Publication Data

US 2015/0126678 A1  May 7, 2015

(30) Foreign Application Priority Data

May 23, 2012  (EP) .................... 12169150

(51) Int. Cl.
*C08G 18/83* (2006.01)
*C09J 175/08* (2006.01)
*C08G 18/75* (2006.01)
*C09J 175/04* (2006.01)
*C07F 7/18* (2006.01)
*C08G 18/10* (2006.01)
*C08G 18/28* (2006.01)
*C08G 18/48* (2006.01)
*C08G 18/76* (2006.01)
*C08G 18/71* (2006.01)

(52) U.S. Cl.
CPC .......... *C08G 18/837* (2013.01); *C07F 7/1804* (2013.01); *C08G 18/10* (2013.01); *C08G 18/285* (2013.01); *C08G 18/289* (2013.01); *C08G 18/4866* (2013.01); *C08G 18/718* (2013.01); *C08G 18/755* (2013.01); *C08G 18/7621* (2013.01); *C09J 175/04* (2013.01); *C09J 175/08* (2013.01); *C08G 2190/00* (2013.01)

(58) Field of Classification Search
CPC ...... C07F 7/1804; C07F 7/1836; C07F 7/184; C08G 18/10; C08G 18/289; C08G 18/718; C08G 18/837; C08G 2190/00; C09J 175/04; C09J 175/08
See application file for complete search history.

(56) References Cited

U.S. PATENT DOCUMENTS

| 5,587,502 | A | 12/1996 | Moren et al. |
| 7,956,209 | B2 | 6/2011 | Laas et al. |
| 2011/0034627 | A1* | 2/2011 | Boudet ................. C08G 18/10 524/588 |
| 2013/0272979 | A1* | 10/2013 | Nguyen .................. A61Q 5/06 424/60 |

FOREIGN PATENT DOCUMENTS

DE   10 2007 032 666 A1   1/2009

OTHER PUBLICATIONS

Abstract of SU 555 104 A1 (Aug. 25, 1977).
International Search Report issued in International Patent Application No. PCT/EP2013/060553 dated May 27, 2014 (with translation).
Jan. 31, 2017 Office Action issued in Japanese Patent Application No. 2015-513166.

* cited by examiner

*Primary Examiner* — Rabon Sergent
(74) *Attorney, Agent, or Firm* — Oliff PLC

(57) ABSTRACT

Methods for producing a polymer with end groups of formula (I), which is free of isocyanate groups,

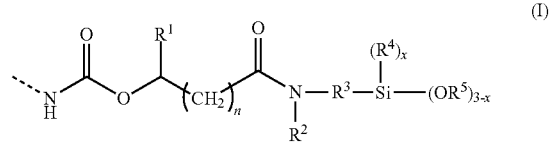

wherein at least one hydrosilane of formula (II) is reacted with at least one polyurethane polymer containing isocyanate groups,

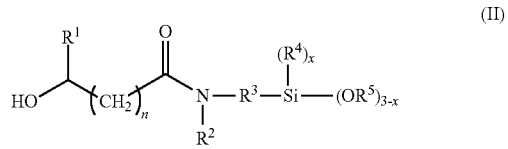

where $R^1$ stands for an alkyl group having 1 to 12 C atoms, $R^2$ stands for a hydrogen atom or for an alkyl group having 1 to 12 C atoms, which optionally comprises ether oxygen or amine nitrogen, $R^3$ stands for a linear or a branched alkylene or cycloalkylene residue having 1 to 20 C atoms, optionally with aromatic parts, and optionally with one or more heteroatoms, $R^4$ stands for an alkyl group having 1 to 6 C atoms, $R^5$ stands for an alkyl group having 1 to 10 C atoms, which optionally comprises one or more ether oxygens, n stands for 2 or 3 or 4, and x stands for 0 or 1.

8 Claims, No Drawings

POLYMER CONTAINING SILANE GROUPS

TECHNICAL FIELD

The invention relates to polymers containing silane groups and to their use as component of moisture curing compositions, particularly for adhesive bonding, sealing and coating of construction and industry products.

PRIOR ART

Polymers containing silane groups, also referred to as "silane functional polymers" or "silane terminated polymers" or "STP," have been used for some time successfully as binder system in moisture curing compositions which are used, in particular, as isocyanate free elastic adhesives, sealants and coatings in the construction and manufacturing industry. One pathway that can be implemented easily to obtain polymers containing silane groups, and that starts with commonly available raw materials and is thus commercially attractive, passes through the reaction of aminosilanes with polyurethane polymers containing isocyanate groups, wherein the silane groups in the end are bound via urea groups to the polymer. However, the polymers containing silane groups that can be obtained in this manner have a rather high viscosity, which makes it difficult to formulate compositions that have good processability and which limits their resistance to thermal stress in the cured state in the temperature range of 80° C. or higher.

Interesting properties pertaining to viscosity and heat resistance are presented by polymers containing silane groups, the silane groups of which are bound to the polymer via urethane groups instead of urea groups. Such polymers containing silane groups are known as reaction products of polyols with isocyanatosilanes. However, this pathway is of only limited interest, since isocyanatosilanes are expensive, not very storable, and strongly toxic. The reaction of polyurethane polymers containing isocyanate groups with hydroxysilanes would be more attractive.

U.S. Pat. No. 5,587,502 discloses silanes that comprise hydroxyl groups and are obtained by reacting aminosilanes with cyclic alkylene carbonates, and polymers containing silane groups and are obtained from them. However, these polymers containing silane groups also have an unsatisfactory heat resistance.

DESCRIPTION OF THE INVENTION

The problem of the present invention therefore is to provide a polymer containing silane groups which has a low viscosity and which cures under the effect of moisture to form a resilient material with a good heat resistance.

It was found surprisingly that a polymer according to Claim 1 solves this problem. It has a low viscosity and an excellent storage stability and it cures rapidly under the effect of moisture to form a resilient material with good strength, extensibility and heat resistance. The polymer can be produced surprisingly selectively by a simple method starting with polyurethane polymers containing isocyanate groups and with special hydroxysilanes with secondary OH group.

Further aspects of the invention are the subject matter of additional independent claims. Particularly preferred embodiments of the invention are the subject matter of the dependent claims.

Ways of Implementing the Invention

The subject matter of the invention is a polymer with end groups of formula (I), which is free of isocyanate groups,

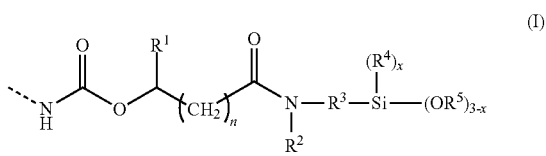

where
$R^1$ stands for an alkyl group having 1 to 12 C atoms;
$R^2$ stands for a hydrogen atom or for an alkyl group having 1 to 12 C atoms, which optionally comprises ether oxygen or amine nitrogen;
$R^3$ stands for a linear or branched alkylene or cycloalkylene residue having 1 to 12 C atoms, optionally with aromatic parts, and optionally with one or more heteroatoms, in particular nitrogen atoms;
$R^4$ stands for an alkyl group having 1 to 6 C atoms;
$R^5$ stands for an alkyl group having 1 to 10 C atoms, which optionally comprises one or more ether oxygens;
n stands for 2 or 3 or 4; and
x stands for 0 or 1.

In the present document, the term "silane" or "organosilane" denotes compounds that, on the one hand, comprise one, usually two or three, alkoxy groups bound via Si—O bonds directly to the silicon atom, and, on the other hand, comprise at least one organic residue bound via a Si—C bond directly to the silicon atom. Accordingly, the term "silane group" denotes a silane which is bound via its organic residue.

The terms "aminosilane," hydroxysilane," "isocyanatosilane," and the like denote organosilanes that comprise, on the organic residue, a corresponding functional group, that is to say an amino group, hydroxyl group or isocyanate group.

Substance names starting with "poly," such as polyol or polyisocyanate, denote substances that formally contain two or more of the functional groups occurring in their name per molecule.

The term "polyurethane polymer" includes all the polymers that are produced by the so-called diisocyanate polyaddition method. The term "polyurethane polymer" also includes polyurethane polymers comprising isocyanate groups, as can be obtained by reacting polyisocyanates and polyols and which themselves represent polyisocyanates and are also often referred to as prepolymers.

In the present document, the term "molecular weight" of oligomers or polymers denotes the average molecular weight $M_n$ (number average), which is typically determined by GPC against polystyrene as standard.

The end groups of formula (I) are silane groups. Silane groups have the property of hydrolyzing in contact with moisture. In the process, silanol groups (Si—OH groups) form and, due to subsequent condensation reactions, siloxane groups (Si—O—Si groups) form.

$R^1$ preferably stands for a linear alkyl group having 2 to 8, in particular 4 to 6, C atoms. Such a polymer has a particularly low viscosity and a particularly good storage stability.

Moreover, $R^1$ preferably stands for a methyl group. Such a polymer allows particularly high strengths and particularly good heat resistances.

It is particularly preferable for the residue $R^1$ to stand for a residue $R^{1a}$, where $R^{1a}$ stands for n-butyl, n-pentyl, n-hexyl, n-heptyl or n-octyl, in particularly for n-butyl, n-pentyl or n-hexyl. Such a polymer has a particularly low viscosity and a particularly good storage stability, and it allows particularly good heat resistances.

$R^2$ preferably stands for a hydrogen atom. Such a polymer is particularly easily accessible and allows a particularly good heat resistance.

$R^3$ preferably stands for a linear or branched alkylene residue having 1 to 6 C atoms.

The residue $R^3$ is particularly preferably selected from the group consisting of 1,3-propylene, 2-methyl-1,3-propylene, 1,4-butylene, 3-methyl-1,4-butylene and 3,3-dimethyl-1,4-butylene. Among those, 1,3-propylene and 3,3-dimethyl-1, 4-butylene, in particular 1,3-propylene, are particularly preferable.

$R^4$ preferably stands for a methyl group.

$R^5$ preferably stands for a methyl group or an ethyl group or a hept-3,6-dioxa-1-yl group, particularly preferably for a methyl group or an ethyl group.

n preferably stands for 2 or 3, in particular for 2.

The polymers with these preferred residues $R^3$, $R^4$, $R^5$ and n are derived from hydroxysilanes that are particularly easily accessible.

$R^5$ stands particularly preferably for an ethyl group. These polymers are particularly storage-stable and during their curing they do not cleave off methanol, which is advantageous for toxicological reasons.

x preferably stands for 0. These polymers hydrolyze particularly rapidly in contact with moisture and allow good mechanical properties.

It is preferable for the polymer with end groups of formula (I) to have a molecular weight in the range from 1000 to 30,000 g/mol, preferably 2000 to 25,000 g/mol, particularly preferably 3000 to 20,000 g/mol, and in particular from 4000 to 15,000 g/mol. Such a polymer allows good mechanical properties.

It is preferable for the polymer with end groups of formula (I) to comprise mostly polyoxyalkylene units, particularly preferably polyoxyethylene and/or polyoxypropylene units, in particular polyoxypropylene units. Such a polymer has a low viscosity and it allows good mechanical properties.

Most of the end groups of formula (I) are in particular bound to cycloaliphatic residues. Such a polymer has particularly low viscosities and it is particularly light-stable.

The polymer preferably comprises 1 to 4, particularly preferably 1 to 3, in particular 2 or 3, most preferably 2, end groups of formula (I). Such a polymer has good mechanical properties, in particular a high extensibility.

Moreover, the present invention relates to a method for producing a polymer with end groups of formula (I) by reacting at least one hydroxysilane of formula (II) with at least one polyurethane polymer containing isocyanate groups.

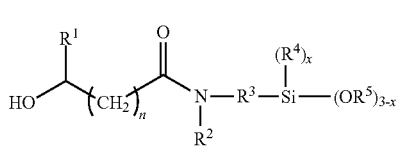

(II)

In formula (II), $R^1$, $R^2$, $R^3$, $R^4$, $R^5$, n and x have the already indicated meanings.

In this reaction, the hydroxyl groups are used at least in a stoichiometric ratio, particularly in a slightly over stoichiometric ratio, with respect to the isocyanate groups. In particular, an OH/NCO ratio from 1.0 to 1.25 is used. The reaction is preferably carried out at a temperature in the range from 20° C. to 120° C., in particular 50° C. to 100° C. It is preferable to use at least one catalyst here, in particular a bismuth(III), zinc(II) or tin(II) compound or an organotin compound.

An additional subject matter of the present invention is a hydroxysilane of formula (II a), which represents a preferred hydroxysilane of formula (II).

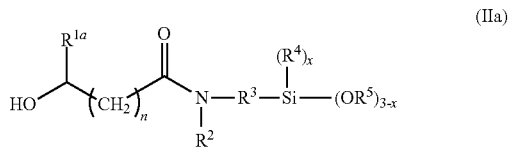

(IIa)

In formula (II a), $R^{1a}$ stands for n-butyl, n-pentyl, n-hexyl, n-heptyl or n-octyl, in particular for n-butyl, n-pentyl or n-hexyl; and $R^2$, $R^3$, $R^4$, $R^5$, n and x have the already indicated meanings.

The hydroxysilane of formula (II a) has special advantages. It can be produced surprisingly selectively from barely toxic, easily accessible starting materials by a simple method, and it has a particularly low tendency to undergo self condensation. Starting from it, particularly low-viscosity, storage-stable polymers with end groups of formula (I) are accessible.

The hydroxysilane of formula (II a) is preferably selected from the group consisting of N-(3-trimiethoxysilylpropyl)-4-hydroxyoctanamide, N-(3-triethoxysilyipropyl)-4-hydroxyoctanamide. N-(2,2-dimethyl-4-trimethoxysilylbutyl)-4-hydroxyoctanamide, N-(2,2-dimethyl-4-triethoxysilylbutyl)-4-hydroxyoctanamide, N-(3-trimethoxysilyipropyl)-4-hydroxynonanamide, N-(3-triethoxysilytpropyl)-4-hydroxynonanamide, N-(2,2-dimethyl-4-trimethoxysilylbutyl)-4-hydroxynonanamide, N-(2,2-dimethyl-4-triethoxysilylbutyl)-4-hydroxynonanamide, N-(3-trimethoxysilylpropyl)-4-hydroxydecanamide, N-(3-triethoxysilylpropyl)-4-hydroxydecanamide, N-(2,2-dimethyl-4-trimethoxysilylbutyl)-4-hydroxydecanamide, N-(2,2-dimethyl-4-triethoxysilylbutyl)-4-hydroxydecanamide, N-(3-trimethoxysilylpropyl)-4-hydroxyundecanamide, N-(3-triethoxysilylpropyl)-4-hydroxyundecanamide, N-(2,2-dimethyl-4-trimethoxysilylbutyl)-4-hydroxyundecanamide, N-(2,2-dimethyl-4-triethoxysilylbutyl)-4-hydroxyundecanamide, N-(3-trimethoxysilylpropyl)-4-hydroxydodecanamide, N-(3-triethoxysilylpropyl)-4-hydroxydodecanamide, N-(2,2-dimethyl-4-trimethoxysilylbutyl)-4-hydroxydodecanamide, N-(2,2-dimethyl-4-triethoxysilylbutyl)-4-hydroxydodecanamide, N-(3-trimethoxysilylpropyl)-5-hydroxynonanamide, N-(3-triethoxysilylpropyl)-5-hydroxynonanamide, N-(2,2-dimethyl-4-trimethoxysilylbutyl)-5-hydroxynonanamide, N-(2, 2-dimiethyl-4-triethoxysilylbutyl)-5-hydroxynonanamiide, N-(3-trimiethoxysilylpropyl)-5-hydroxydecanamide, N-(3-triethoxysilylpropyl)-5-hydroxydecanamide, N-(2,2-dimethyl-4-trimethoxysilylbutyl)-5-hydroxydecanamide N-(2, 2-dimethyl-4-triethoxysilylbutyl)-5-hydroxydecanamide, N-(3-trimethoxysilylpropyl)-5-hydroxyundecanamide, N-(3-triethoxysilylpropyl)-5-hydroxyundecanamide, N-(2, 2-dimethyl-4-trimethoxysilylbutyl)-5-hydroxyundecanamide, N-(2,2-dimethyl-4-triethoxysilylbutyl)-5-hydroxyundecanamide, N-(3-trimethoxysilylpropyl)-5-hydroxydodecanamide, N-(3-triethoxysilylpropyl)-5-hydroxydodecanamide, N-(2,2-dimethyl-4-trimethoxysilylbutyl)-5-hydroxydodecanamide, N-(2,2- dimethyl-4-triethoxysilylbutyl)-5-hydroxydodecanamide, N-(3-trimethoxysilylpropyl)-6-hydroxydecanamide, N-(3-triethoxysilylpropyl)-6-hydroxydecanamide, N-(2,2-dimethyl-4-trimethoxysilylbutyl)-5-hydroxydecanamide, N-(2,2-dimethyl-4-triethoxysilylbutyl)-6-hydroxydecanamide, N-(3-trimethoxysilylpropyl)-6-hydroxyundecanamide, N-(3-triethoxysilylpropyl)-6-hydroxyundecanamide, N-(2,2-dimethyl-4-trimethoxysilylbutyl)-6-hydroxyundecanamide, N-(2,2-dimethyl-4-triethoxysilylbutyl)-6-hydroxyundecanamide, N-(3-trimethoxysilylpropyl)-6-hydroxydodecanamide, N-(3-triethoxysilylpropyl)-6-hydroxydodecanamide, N-(2,2-dimethyl-4-trimethoxysilylbutyl)-6-hydroxydodecanamide and N-(2,2-dimethyl-4-triethoxysilylbutyl)-6-hydroxydodecanamide.

The silylpropyl compounds are particularly preferable. These hydroxysilanes are particularly easily accessible.

Moreover, it is particularly preferable to use compounds in which the OH group is in position 4 or 5, in particular in position 4. These hydroxysilanes are particularly easily accessible.

Moreover, the triethoxysilyl compounds are particularly preferable. These hydroxysilanes are particularly storage-stable and they do not release methanol.

A polyurethane polymer containing isocyanate groups that is suitable for the reaction with at least one hydroxysilane of formula (II) is obtained in particular by reacting at least one polyol with at least one polyisocyanate, in particular a diisocyanate. This reaction can occur by causing the polyol and the polyisocyanate to react by the usual methods, in particular at temperatures from 50° C. to 100° C., optionally with the co-use of suitable catalysts, wherein the polyisocyanate is dosed in such a way that its isocyanate groups are present in stoichiometric excess in relation to the hydroxyl groups of the polyol. In particular, the excess of polyisocyanate is selected so that, in the resulting polyurethane polymer, after the reaction of all the hydroxyl groups of the polyol, a content of free isocyanate groups of 0.1-5 wt %, preferably 0.1-2.5 wt, particularly preferably 0.2-1 wt %, relative to the entire polymer, remains. Preferred polyurethane polymers with the mentioned content of free isocyanate groups are those obtained by reacting diisocyanates with high molecular weight diols in a NCO/OH ratio from 1.5/1 to 2.2/1, in particular 1.8/1 to 2.0/1. Optionally, the polyurethane polymer can be prepared with the co-use of plasticizers, wherein the plasticizers used contain no groups that react with isocyanates.

As polyol for the preparation of a polyurethane polymer containing isocyanate groups, the following commercial polyols or any mixtures thereof are particularly suitable:

polyoxyalkylene polyols, also referred to as polyether polyols or oligoetherols, which are polymerization products of ethylene oxide, 1,2-propylene oxide, 1,2- or 2,3-butylene oxide, oxetan, tetrahydrofuran or mixtures thereof, possibly polymerized by means of a starter molecule with two or more active hydrogen atoms, such as, for example, water, ammonia, or compounds with several OH or NH groups, such as, for example, 1,2-ethanediol, 1,2- and 1,3-propanediol, neopentyl glycol, diethylene glycol, triethylene glycol, the isomeric dipropylene glycols and tripropylene glycols, the isomeric butanediols, pentanediols, hexanediols, heptanediols, octanediols, nonanediols, decanediols, undecanediols, 1,3- and 1,4-cyclohexanedimethanol, bisphenol A, hydrogenated bisphenol A, 1,1,1-trimethylolethane, 1,1,1-trimethylolpropane, glycerol, aniline, as well as mixtures of the above-mentioned compounds. Preferable polyoxyalkylenepolyols are those having a low unsaturation degree (measured according to ASTM D-2849-69 and indicated in milliequivalent unsaturation per gram polyol (mEq/g)), prepared, for example, using so-called double metal cyanide complex catalysts (DMC catalysts).

Particularly suitable are polyoxyalkylenediols or polyoxyalkylenetriols, in particular polyoxyethylene- and polyoxypropylenedi- and -triols.

Also particularly preferable are so-called ethylene oxide terminated (EO end capped) polyoxypropylenepolyols. The latter are mixed polyoxyethylene-polyoxypropylene polyols which are obtained, for example, by further alkoxylating polyoxypropylenepolyols with ethylene oxide, after the completion of the polypropoxylation reaction, and which as a result comprise primary hydroxyl groups.

Styrene-acrylonitrile or acrylonitrile-methyl methacrylate-grafted polyether polyols.

Polyester polyols, also referred to as oligoesterols, prepared by known methods, in particular polycondensation of hydroxycarboxylic acids or polycondensation of aliphatic and/or aromatic polycarboxylic acids with bivalent or polyvalent alcohols.

Particularly suitable polyester polyols are those that are prepared from bivalent to trivalent, and in particular bivalent, alcohols, such as, for example, ethylene glycol, diethylene glycol, propylene glycol, dipropylene glycol, neopentyl glycol, 1,4-butanediol, 1,5-pentanediol, 3-methyl-1,5-hexanediol, 1,6-hexanediol, 1,8-octanediol, 1,10-decanediol, 1,12-dodecanediol, 1,12-hydroxystearyl alcohol, 1,4-cyclohexanedimethanol, dimeric fatty acid diol (dimerdiol), hydroxypivalic acid neopentyl glycol ester, glycerol, 1,1,1-trimethylolpropane or mixtures of the above-mentioned alcohols, with organic di- or tricarboxylic acids, in particular dicarboxylic acids, or their anhydrides or esters, such as, for example, succinic acid, glutaric acid, adipic acid, trimethyladipic acid, suberic acid, azelaic acid, sebacic acid, dodecanedicarboxylic acid, maleic acid, fumaric acid, dimer fatty acid, phthalic acid, phthalic acid anhydride, isophthalic acid, terephthalic acid, dimethyl terephthalate, hexahydrophthalic acid, trimellitic acid, and trimellitic acid anhydride, or mixtures of the above-mentioned acids, as well as polyester polyols from lactones, such as, for example, from ε-caprolactone, and starters, such as the above-mentioned bivalent or trivalent alcohols.

Particularly suitable polyester polyols are polyester diols.

Polycarbonate polyols, as prepared by reacting, for example, the above-mentioned alcohols—used for the formation of the polyester polyols—with dialkyl carbonates, diaryl carbonates or phosgene.

Block copolymers carrying at least two hydroxyl groups, and comprising at least two different blocks with polyether, polyester and/or polycarbonate structure of the above-mentioned type, in particular polyether polyester polyols.

Polyacrylate and polymethacrylate polyols.

Polyhydroxy functional fats and oils, for example, natural fats and oils, in particular castor oil, or so-called oleochemical polyols prepared by chemical modification of natural fats and oils, for example, epoxy polyesters or epoxy polyethers prepared by the epoxidation of unsaturated oils and subsequent ring opening with carboxylic acids or alcohols, or polyols obtained by hydroformylation and hydrogenation of unsaturated oils; or polyols obtained by degradation processes such as alcoholysis or ozonolysis and subsequent chemical linking, for example, by transesterification or dimerization of the degradation products thus obtained or derivatives thereof thus obtained. Suitable degradation products of natural fats and oils are in particular fatty acids and fatty alcohols as well as fatty esters, in particular methyl esters (FAME), which can be derivatized, for example, by hydroformylation and hydrogenation to form hydroxy fatty acid esters.

Polyhydrocarbon polyols, also referred to as oligohydrocarbonols, such as, for example, polyhydroxy functional polyolefins, polyisobutylenes, polyisoprenes; polyhydroxy functional ethylene-propylene-, ethylene-butylene- or ethylene-propylene-diene copolymers, as manufactured, for example, by the Kraton Polymers company; polyhydroxy functional polymers of dienes, in particular of 1,3-butadiene, which can also be prepared in particular by anionic polymerization; polyhydroxy functional copolymers of dienes, such as 1,3-butadiene or diene mixtures and vinyl monomers, such as styrene, acrylonitrile, vinyl chloride, vinyl acetate, vinyl alcohol, isobutylene and isoprene, for example, polyhydroxy functional acrylonitrile/butadiene copolymers, such as those that can be prepared, for example, from epoxides or amino alcohols and carboxyl terminated acrylonitrile/butadiene copolymers (available commercially, for example, under the name Hypro® (formerly Hycar®) CTBN and CTBNX and ETBN from Nanoresins AG, Germany, or Emerald Performance Materials LLC); as well as hydrogenated polyhydroxy functional polymers or copolymers of dienes.

As polyol, it is preferably to use polyoxyalkylene polyols, polyester polyols, polycarbonate polyols and polyacrylate polyols. Polyoxyalkylene polyols are particularly preferred.

Preferable polyoxyalkylene polyols are polyoxypropylene polyols and polyoxyethylene-polyoxypropylene mixed polyols.

The polyol preferably has a molecular weight from 1000 to 20,000 g/mol, particularly preferably from 2000 to 20,000 g/mol.

The polyol is preferably a diol.

In addition to these mentioned polyols, small quantities of low molecular weight bivalent or polyvalent alcohols can also be used, such as, for example, 1,2-ethanediol, 1,2- and 1,3-propanediol, neopentyl glycol, diethylene glycol, triethylene glycol, isomeric dipropylene glycols and tripropylene glycols, isomeric butanediols, pentanediols, hexanediols, heptanediols, octanediols, nonanediols, decanediols, undecanediols, 1,3- and 1,4-cyclohexanedimethanol, hydrogenated bisphenol A, dimeric fatty alcohols, 1,1,1-trimethylolethane, 1,1,1-trimethylolpropane, glycerol, pentaerythritol, sugar alcohols, such as xylitol, sorbitol or mannitol, sugars, such as sucrose, other higher valency alcohols, low molecular weight alkoxylation products of the above-mentioned bivalent and polyvalent alcohols, as well as mixtures of the above-mentioned alcohols, in the manufacture of the polyurethane polymer containing isocyanate groups.

Suitable polyisocyanates for the preparation of a polyurethane polymer containing isocyanate groups are in particular the following commercial polyisocyanates or any mixtures thereof:

aliphatic isocyanates, such as, in particular, 1,4-tetramethylene diisocyanate, 2-methylpentamethylene-1,5-diisocyanate, 1,6-hexamethylene diisocyanate (HDI), 2,2,4- and 2,4,4-trimethyl-1,6-hexamethylene diisocyanate (TMDI), 1,10-decamethylene diisocyanate, 1,12-dodecamethylene diisocyanate, lysine and lysine ester diisocyanate, cyclohexane-1,3- and -1,4-diisocyanate, 1-methyl-2,4- and -2,6-diisocyanatocyclohexane and any mixtures of these isomers (HTDI or H$_6$TDI), 1-isocyanato-3,3,5-trimethyl-5-isocyanatomethylcyclohexane (=isophorone diisocyanate or IPDI), perhydro-2,4'- and -4,4'-diphenylmethane diisocyanate (HMDI or H$_{12}$MDI), 1,4-diisocyanato-2,2,6-trimethylcyclohexdane (TMCDI), 1,3- and 1,4-bis-(isocyanatomethyl)cyclohexane, m- and p-xylylene diisocyanate (m- and p-XDI), tetramethyl-1,3- and -1,4-xylylene diisocyanate (m- and p-TMXDI), bis-(1-isocyanato-1-methylethyl)naphthaline, dimer and trimer fatty acid isocyanates, such as 3,6-bis-(9-isocyanatononyl)-4,5-di-(1-heptenyl)cyclohexene (dimeryl diisocyanate) and α,α,α',α',α'',α''-hexamethyl-1,3-5-mesitylene triisocyanate, as well as moreover aromatic isocyanates, such as, in particular, 2,4- and 2,6-toluylene diisocyanate and any mixtures of these isomers (TDI), 4,4'-, 2,4'- and 2,2'-diphenylmethane diisocyanate and any mixtures of these isomers (MDI), mixtures of MDI and MDI homologs (polymeric MDI or PMDI), 1,3- and 1,4-phenylene diisocyanate, 2,3,5,6-tetramethyl-1,4-diisocyanatobenzene, naphthaline-1,5-diisocyanate (NDI), 3,3'-dimethyl-4,4'-diisocyanatodiphenyl (TODI), dianisidine diisocyanate (DADI), 1,3,5-tris-(isocyanatomethyl)benzene, tris-(4-isocyanatophenyl)methane and tris-(4-isocyanatophenyl)thiophosphate, as well as oligomers and polymers of the above-mentioned isocyanates, as well as any mixtures of the above-mentioned isocyanates.

Preferred polyisocyanates are diisocyanate. IPDI, HDI, MDI and TDI, in particular IPDI, are particularly preferred. On the basis of IPDI, polymers with end groups of formula (I) can be produced, which have a low viscosity and which allow good mechanical properties and a low yellowing tendency.

An additional possibility for producing a polymer with end groups of formula (I) is the reaction of at least one hydroxysilane of formula (II) with at least one diisocyanate $R^6$—(NCO)$_2$ to form an isocyanatosilane of formula (III) and the subsequent reaction of this isocyanatosilane with at least one polyol.

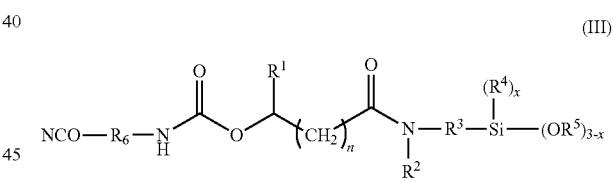

(III)

In formula (III), $R^6$ stands for a bivalent hydrocarbon residue having 4 to 16 C atoms, and $R^1$, $R^2$, $R^3$, $R^4$, $R^5$, n and x have the already indicated meanings.

$R^6$ preferably stands for 1,6-hexylene, 2,2,4- and 2,4,4-trimethyl-1,6-hexylene, 1,3- and 1,4-cyclohexylene, 1,3- and 1,4-xylylene, 1,3- and 1,4-tetramethylxylylene, 4,4'- and 2,4'-substituted diphenylmethane, 2,4- and 2,6-substituted toluene and IPDI after removal of the two isocyanate groups, in particular for IPDI after removal of the two isocyanate groups. These isocyanatosilanes represent easily accessible, storage-stable substances.

The OH groups of the polyol are preferably used approximately stoichiometrically relative to the isocyanate groups of the isocyanatosilane of formula (III).

As polyol, it is particularly suitable to use the polyols mentioned already for the preparation of a polyurethane polymer containing isocyanate groups.

Polyoxyalkylene polyols, polyester polyols, polycarbonate polyols and polyacrylate polyols are preferred. Particularly preferable are polyoxyalkylene polyols. Preferred polyoxyalkylene polyols are polyoxypropylene polyols and polyoxyethylene-polyoxypropylene mixed polyols.

The polyol preferably has a molecular weight from 2000 to 20,000 g/mol.

The polyol is preferably a diol.

An additional subject matter of the present invention is an isocyanatosilane of formula (III a), which represents a reaction product of at least one hydroxysilane of formula (II a) with at least one diisocyanate $R^6$—$(NCO)_2$.

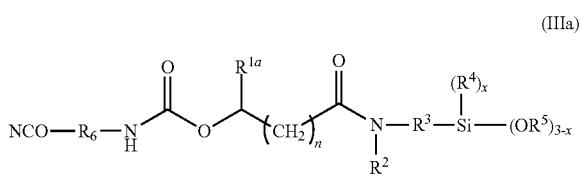

(IIIa)

In formula (III a), $R^{1a}$, $R^2$, $R^3$, $R^4$, $R^5$, $R^6$, n and x have the already mentioned meanings.

As diisocyanate $R^6$—$(NCO)_2$, it is suitable to use the diisocyanates already mentioned for the preparation of a polyurethane polymer containing isocyanate groups.

Particularly suitable are 1,6-hexamethylene diisocyanate, 2,2,4- and 2,4,4-trimethyl-1,6-hexamethylene diisocyanate, cyclohexane-1,3- and -1,4-diisocyanate, I-isocyanato-3,3,5-trimethyl-5-isocyanatomethylcyclohexane, m- and p-xylylene diisocyanate, tetramethyl-1,3- and -1,4-xylylene diisocyanate, 4,4'- and 2,4'-diphenylmethane diisocyanate and 2,4- and 2,6-toluylene diisocyanate.

Among those, it is preferable to use 1,6-hexamethylene diisocyanate, 1-isocyanato-3,3,5-trimethyl-5-isocyanatomethylcyclohexane, 4,4'- and 2,4'-diphenylmethane diisocyanate, and 2,4- and 2,6-toluylene diisocyanate.

1-Isocyanato-3,3,5-trimethyl-5-isocyanatomethylcyclohexane is particularly preferable.

Particularly preferable isocyanatosilanes of formula (III a) are selected from the group consisting, of 1-oxo-1-((3-(trimethoxysilyl)propyl)amino)-4-octyl ((5-isocyanato-1,3,3-trimethylcyclohexyl)methyl)carbamate; 1-oxo-1-((3-(triethoxysilyl)propyl)amino)-4-octyl((5-isocyanato-1,3,3-trimethylcyclohexyl)methyl)carbamate; 1-oxo-1-((2,2-dimethyl-4-(trimethoxysilyl)butyl)amino)-4-octyl ((5-isocyanato-1,3,3-trimethylcyclohexyl)methyl)carbamate; 1-oxo-1-((2,2-dimethyl-4-(triethoxysilyl)butyl)amino)-4-octyl ((5-isocyanato-1,3,3-trimethylcyclohexyl)methyl)carbamate; 1-oxo-1-((3-(trimiethoxysilyl)propyl)amino)-4-nonyl((5-isocyanato-1,3,3-trimethylcyclohexyl)methyl)carbamate; 1-oxo-1-((3-(triethoxysilyl)propyl)amino)-4-nonyl ((5-isocyanato-1,3,3-trimethylcyclohexyl)methyl)carbamate; 1-oxo-1-((2,2-dimethyl-4-(trimethoxysilyl)butyl)amino)-4-nonyl ((5-isocyanato-1,3,3-trimethylcyclohexyl)methyl)carbamate; 1-oxo-1-((2,2-dimethyl-4-(triethoxysilyl)butyl)amino)-4-nonyl ((5-isocyanato-1,3,3-trimethylcyclohexyl)methyl)carbamate; 1-oxo-1-((3-(trimethoxysilyl)propyl)amino)-4-decyl((5-isocyanato-1,3,3-trimethylcyclohexyl)methyl)carbamate; 1-oxo-1-((3-(triethoxysilyl)propyl)amino)-4-decyl ((5-isocyanato-1,3,3-trimethylcyclohexyl)methyl)carbamate; 1-oxo-1-((2,2-dimethyl-4-(trimethoxysilyl)butyl)amino)-4-decyl ((5-isocyanato-1,3,3-trimethylcyclohexyl)methyl)carbamate; 1-oxo-1-((2,2-dimethyl-4-(triethoxysilyl)butyl)amino)-4-decyl ((5-isocyanato-1,3,3-trimethylcyclohexyl)methyl)carbamate; 1-oxo-1-((3-(trimethoxysilyl)propyl)amino)-4-undecyl ((5-isocyanato-1,3,3-trimethylcyclohexyl)methyl)carbamate; 1-oxo-1-((3-(triethoxysilyl)propyl)amino)-4-undecyl ((5-isocyanato-1,3,3-trimethylcyclohexyl)methyl)carbamate; 1-oxo-1-((2,2-dimethyl-4-(trimethoxysilyl)butyl)amino)-4-undecyl ((5-isocyanato-1,3,3-trimethylcyclohexyl)methyl)carbamate, 1-oxo-1-((2,2-dimethyl-4-(triethoxysilyl)butyl)amino)-4-undecyl ((5-isocyanato-1,3,3-trimethylcyclohexyl)methyl)carbamate; 1-oxo-1-((3-(trimethoxysilyl)propyl)amino)-4-dodecyl ((5-isocyanato-1,3,3-trimethylcyclohexyl)methyl)carbamate; 1-oxo-1-((3-(triethoxysilyl)propyl)amino)-4-dodecyl ((5-isocyanato-1,3,3-trimethylcyclohexyl)methyl)carbamate; 1-oxo-1-((3-(triethoxysilyl)propyl)amino)-4-dodecyl((5-isocyanato-1,3,3-trimethylcyclohexyl)methyl)carbamate; 1-oxo-1-((2,2-dimethyl-4-(trimethoxysilyl)butyl)amino)-4-dodecyl ((5-isocyanato-1,3,3-trimethylcyclohexyl)methyl)carbamate; 1-oxo-1-((2,2-dimethyl-4-(triethoxysilyl)butyl)amino)-4-dodecyl ((5-isocyanato-1,3,3-trimethylcyclohexyl)methyl)carbamate, 1-oxo-1-((3-(trimethoxysilyl)propyl)amino)-5-nonyl((5-isocyanato-1,3,3-trimethylcyclohexyl)methyl)carbamate; 1-oxo-1-((3-(triethoxysilyl)propyl)amino)-5-nonyl ((5-isocyanato-1,3,3-trimethylcyclohexyl)methyl)carbamate; 1-oxo-1-((2,2-dimethyl-4-(trimethoxysilyl)butyl)amino)-5-nonyl ((5-isocyanato-1,3,3-trimethylcyclohexyl)methyl)carbamate; 1-oxo-1-((2,2-dimethyl-4-(triethoxysilyl)butyl)amino)-5-nonyl ((5-isocyanato-1,3,3-trimethylcyclohexyl)methyl)carbamate; 1-oxo-1-((3-(trimethoxysilyl)propyl)amino)-5-decyl((5-isocyanato-1,3,3-trimethylcyclohexyl)methyl)carbamate; 1-oxo-1-((3-(triethoxysilyl)propyl)amino)-5-decyl ((5-isocyanato-1,3,3-trimethylcyclohexyl)methyl)carbamate; 1-oxo-1-(2,2-dimethyl-4-(trimethoxysilyl)butyl)amino)-5-decyl ((5-isocyanato-1,3,3-trimethylcyclohexyl)methyl)carbamate; 1-oxo-1-((2,2-dimethyl-4-(triethoxysilyl)butyl)amino)-5-decyl ((5-isocyanato-1,3,3-trimethylcyclohexyl)methyl)carbamate; 1-oxo-1-((3-(trimethoxysilyl)propyl)amino)-5-undecyl ((5-isocyanato-1,3,3-trimethylcyclohexyl)methyl)carbamate; 1-oxo-1-((3-(triethoxysilyl)propyl)amino)-5-undecyl ((5-isocyanato-1,3,3-trimethylcyclohexyl)methyl)carbamate; 1-oxo-1-((2,2-dimethyl-4-(trimethoxysilyl)butyl)amino)-5-undecyl ((5-isocyanato-1,3,3-trimethylcyclohexyl)methyl)carbamate; 1-oxo-1-((2,2-dimethyl-4-(triethoxysilyl)butyl)amino)-5-undecyl ((5-isocyanato-1,3,3-trimethylcyclohexyl)methyl)carbamate; 1-oxo-1-((3-(trimethoxysilyl)propyl)amino)-5-dodecyl ((5-isocyanato-1,3,3-trimethylcyclohexyl)methyl)carbamate; 1-oxo-1-((3-(triethoxysilyl)propyl)amino)-5-dodecyl ((5-isocyanato-1,3,3-trimethylcyclohexyl)methyl)carbamate; 1-oxo-1-((2,2-dimethyl-4-(trimethoxysilyl)butyl)amino)-5-dodecyl ((5-isocyanato-1,3,3-trimethylcyclohexyl)methyl)carbamate; 1-oxo-1-((2,2-dimethyl-4-(triethoxysilyl)butyl)amino)-5-dodecyl ((5-isocyanato-1,3,3-trimethylcyclohexyl)methyl)carbamate; 1-oxo-1-((3-(trimiethoxysilyl)propyl)amino)-6-decyl((5-isocyanato-1,3,3-trimethylcyclohexyl)methyl)carbamate; 1-oxo-1-((3-(triethoxysilyl)propyl)amino)-6-decyl ((5-isocyanato-1,3,3-trimethylcyclohexyl)methyl)carbamate; 1-oxo-1-((2,2-dimethyl-4-(trimethoxysilyl)butyl)amino)-6-decyl ((5-isocyanato-1,3,3-trimethylcyclohexyl)methyl)carbamate; 1-oxo-1-((2,2-dimethyl-4-(triethoxysilyl)butyl)amino)-6-decyl ((5-isocyanato-1,3,3-trimethylcyclohexyl)methyl)carbamate; 1-oxo-1-((3-(trimethoxysilyl)propyl)amino)-6-undecyl ((5-isocyanato-1,3,3-trimethylcyclohexyl)methyl)carbamate; 1-oxo-1-((3-(triethoxysilyl)propyl)amino)-6-undecyl ((5-isocyanato-1,3,3-trimethylcyclohexyl)methyl)carbamate; 1-oxo-1-((2,2-dimethyl-4-(trimethoxysilyl)butyl)amino)-6-undecyl ((5-isocyanato-1,3,3-trimethylcyclohexyl)methyl)carbamate; 1-oxo-1-((2,2-dimethyl-4-(triethoxysilyl)butyl)

amino)-6-undecyl ((5-isocyanato-1,3,3-trimethylcyclohexyl)methyl)carbamate; 1-oxo-1-((3-(trimethoxysilyl)propyl)amino)-6-dodecyl ((5-isocyanato-1,3,3-trimethylcyclohexyl)methyl)carbamate; 1-oxo-1-((3-(triethoxysilyl)propyl)amino)-6-dodecyl ((5-isocyanato-1,3,3-trimethylcyclohexyl)methyl)carbamate; 1-oxo-1-((2,2-dimethyl-4-(trimethoxysilyl)butyl)amino)-6-dodecyl ((5-isocyanato-1,3,3-trimethylcyclohexyl)methyl)carbamate and 1-oxo-1-((2,2-dimethyl-4-(triethoxysilyl)butyl)amino)-6-dodecyl ((5-isocyanato-1,3,3-trimethylcyclohexyl)methyl)carbamate.

The silylpropyl compounds are particularly preferable. These isocyanatosilanes are particularly easily accessible.

Particularly preferable are moreover the compounds substituted in position 4 and in position 5 on the carbamate oxygen, particularly the compounds substituted in position 4. These isocyanatosilanes are particularly easily accessible.

Particularly preferable are moreover the triethoxysilyl compounds. These isocyanatosilanes are particularly storage-stable and they do not release methanol.

A hydroxysilane of formula (II) can be produced advantageously by reacting at least one lactone of formula (IV) with at least one aminosilane of formula (V).

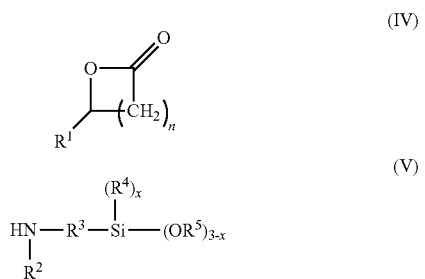

In formulas (IV) and (V), $R^1$, $R^2$, $R^3$, $R^4$, $R^5$, n and x have the already indicated meanings.

This reaction is carried out preferably at temperatures in the range from 50° C. to 150° C., in particular 60° C. to 140° C. In the reaction, a catalyst can be used, in particular an acid, preferably a carboxylic acid. The aminosilane of formula (V) is used preferably approximately stoichiometrically relative to the lactone of formula (IV). In particular, the reaction is carried out with an aminosilane/lactone ratio from 0.8 to 1.1. The reaction can be run without solvent or in a suitable solvent. After the reaction, it is preferable to remove from the reaction product by distillation any volatile compounds present, in particular any solvent present, unreacted starting materials or released methanol or ethanol.

The special structure of the lactone of formula (IV) has a great influence on the course of the reaction. Starting with lactones of formula (IV), the corresponding hydroxysilane of formula (II) is obtained at high yield, in particular with the preferred substituents $R^{1a}$ as $R^1$. On the other hand, if unsubstituted lactones such as γ-butyrolactone, δ-valerolactone or ε-caprolactone are used, reaction products are obtained whose content of hydroxysilane is strongly reduced as a result of self condensation reactions. Such reaction products, which typically include, in addition to other self condensation products, an increased content of cyclic silane compounds of formula (VI), are not well suited for the preparation of polymers containing silane groups.

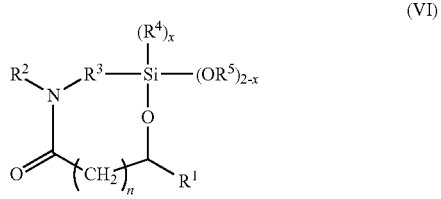

In formula (VI), $R^1$, $R^2$, $R^3$, $R^4$, $R^5$, n and x have the already indicated meanings.

Suitable lactones of formula (IV) are, in particular, γ-valerolactone, γ-hexalactone, γ-heptalactone, γ-octalactone, γ-nonalactone, γ-decalactone, γ-undecalactone, γ-dodecalactone, δ-hexalactone, δ-heptalactone, δ-octalactone, δ-nonalactone, δ-decalactone, δ-undecalactone, δ-dodecalactone, ε-heptalactone, ε-octalactone, ε-nonalactone, ε-decalactone, ε-undecalactone, and ε-dodecalactone.

Among those, γ-octalactone, γ-nonalactone, γ-decalactone, γ-undecalactone, γ-dodecalactone, δ-nonalactone, δ-decalactone, δ-undecalactone, δ-dodecalactone, ε-decalactone, ε-undecalactone and ε-dodecalactone are preferable.

Among those, the γ- and δ-lactones, in particular the γ-lactones, are particularly preferable.

These lactones are compounds with low toxicity. This is particularly advantageous, in particular also since, due to the presence of lactone residues, no toxicological problems can arise for the hydroxysilanes or polymers with end groups of formula (I) produced therewith.

Suitable aminosilanes of formula (V) are, in particular, aminosilanes with a primary amino group, in particular 3-aminopropyltrimethoxysilane, 3-aminopropyldimethoxymethylsilane, 3-amino-2-methylpropyltrimethoxysilane, 4-aminobutyltrimethoxysilane, 4-aminobutyldimethoxymethylsilane, 4-amino-3-methylbutyltrimethoxysilane, 4-amino-3,3-dimethylbutyltrimethoxysilane, 4-amino-3,3-dimethylbutyldimethoxymethylsilane, 2-aminoethyltrimethoxysilane, 2-aminoethyldimethoxymethylsilane, aminomethyltrimethoxysilane, aminomethyldimethoxymethylsilane, aminomethylmethoxydimethylsilane, 7-amino-4-oxaheptyldimethoxymethylsilane, as well as their analogs with ethoxy groups instead of the methoxy groups on the silicon.

Among those, it is preferable to use 3-aminopropyltrimethoxysilane, 3-aminopropyltriethoxysilane, 3-amino-2-methylpropyltrimethoxysilane, 3-amino-2-methylpropyltriethoxysilane, 4-aminobutyltrimethoxysilane, 4-aminobutyltriethoxysilane, 4-amino-3-methylbutyltrimethoxysilane, 4-amino-3-methylbutyltriethoxysilane, 4-amino-3,3-dimethylbutyltrimethoxysilane, 4-amino-3,3-dimethylbutyltriethoxysilane, 2-aminoethyltrimethoxysilane and 2-aminoethyltriethoxysilane.

Particularly preferable are 3-aminopropyltrimethoxysilane, 3-aminopropyltriethoxysilane, 4-amino-3,3-dimethylbutyltrimethoxysilane and 4-amino-3,3-dimethylbutyltriethoxysilane.

The polymer with end groups of formula (I) has good storage stability with exclusion of moisture. In the case of contact with moisture, the end groups of formula (I) hydrolyze, after which the polymer cures to a crosslinked plastic. Thus, the present invention also relates to a crosslinked plastic, which is obtained by reacting at least one polymer with end groups of formula (I) with moisture.

The polymer with end groups of formula (I) has advantageous properties. Its viscosity is relatively low, which is advantageous for its further processing, for example, as moisture-curing composition; analogous polymers containing silane groups, starting from hydroxysilanes with primary instead of secondary OH group, for example, reaction products of γ-butyrolactone with aminosilanes, typically have higher viscosities. The content of low molecular weight silanes in the polymer with end groups of formula (I) is low, since, during its preparation, for example, from a polyurethane polymer containing isocyanate groups and from the hydroxysilane of formula (II), it is possible to work close to the stoichiometric optimum; this, in contrast to analogous polymers containing silane groups, starting from hydroxysilanes with primary OH group. The polymer with end groups of formula (I) moreover has excellent storage stability and cures under the effect of moisture rapidly to form a resilient material with good strength, extensibility and surprisingly good heat resistance. At a very high temperature of 90° C., the cured polymer also remains resilient even under prolonged exposure to heat, while many prior-art polymers containing silane groups lose all strength or even melt already after a few days.

The polymer with end groups of formula (I) is particularly suitable as component of curable compositions, in particular for the formulation of silane-functional moisture-curing compositions.

An additional subject matter of the present invention is a moisture-curing composition containing at least one polymer with end groups of formula (I) and at least one additional component.

The moisture-curing composition according to the invention preferably has a content of polymer with end groups of formula (I) from 5 to 90 wt %, in particular 10 to 60 wt %.

Particularly suitable additional components are catalysts, crosslinking agents, plasticizers, fillers, pigments, solvents, adhesive promoters, drying agents, rheological adjuncts and stabilizers.

The moisture-curing composition preferably contains at least one catalyst which accelerates the crosslinking of polymers containing silane groups. Suitable for this purpose are in particular metal catalysts and/or nitrogen-containing compounds.

Suitable metal catalysts are compounds of titanium, zirconium, aluminum and tin, in particular organotin compounds, organotitanates, organozirconates and organoaluminates, wherein these metal catalysts comprise in particular alkoxy groups, sulfonate groups, carboxyl groups, dialkyl phosphate groups, dialkyl pyrophosphate groups and diketonate groups. Particularly suitable organotin compounds are dialkyltin oxides, dialkyltin dichlorides, dialkyltin dicarboxylates and dialkyltin diketonates, in particular dibutyltin oxide, dibutyltin dichloride, dibutyltin diacetate, dibutyl dilaurate, dibutyltin diacetylacetonate, dioctyltin oxide, dioctyltin dichloride, dioctyltin diacetate, dioctyltin dilaurate and dioctyltin diacetylacetonate, as well as alkyltin thioesters.

Particularly suitable organotitanatees are the following:
titanium(IV) complex compounds with two 1,3-diketonate ligands, in particular 2,4-pentane dionate (=acetylacetonate), and two alcoholate ligands;
titanium(IV) complex compounds with two 1,3-ketoesterate ligands, in particular ethyl acetoacetate, and two alcoholate ligands;
titanium(IV) complex compounds with one or more amino alcoholate ligands, in particular triethanolamine or 2-((2-aminoethyl)amino)ethanol, and one or more alcoholate ligands;
titanium(IV) complex compounds with four alcoholate ligands;
as well as more highly condensed organotitanates, in particular oligomeric titanium(IV) tetrabutanolate, also referred to as polybutyl titanate;
wherein, as alcoholate ligands, isobutoxy, n-butoxy, isopropoxy, ethoxy and 2-ethylhexoxy are particularly suitable.

Most particularly suitable are bis(ethylacetoacetato)diisobutoxytitanium(IV), bis(ethylacetoacetato)diisopropoxytitanium(IV), bis(acetylacetonato)diisopropoxytitanium(IV), bis(acetylacetonato)diisobutoxytitanium(IV), tris(oxyethyl)amineisopropoxytitanium(IV), bis[tris(oxyethyl)amine]diisopropoxytitanium(IV), bis(2-ethythexane-1,3-dioxy)titanium(IV), tris[2-((2-aminoethyl)amino)ethoxy]ethoxytitanium(IV), bis(neopentyl(diallyl))oxydiethoxytitanium(IV), titanium(IV) tetrabutanolate, tetra-(2-ethylhexyloxy)titanate, tetra-(isopropoxy)titanate and polybutyltitanate. Particularly suitable are the commercially available types Tyzor® AA, GBA, GBO, AA-75, AA-65, AA-105, DC, BEAT, BTP, TE, TnBT, KTM, TOT, TPT or IBAY (all from Du Pont/Dorf Ketal); Tytan PBT, TET, X85, TAA, ET, S2, S4 or S6 (all from TensoChema) and Ken-React® KR® TTS, 7, 9QS, 12, 26S, 33DS, 38S, 39DS, 44, 134S, 138S, 133DS, 158FS or LICA® 44 (all from Kenrich Petrochemicals).

Particularly suitable organozirconates are the commercially available types Ken-React® NZ® 38J, KZ® TPPJ, KZ® TPP, NZ® 01, 09, 12 38, 44 or 97 (all from Kenrich Petrochemicals) and Snapcure® 3020, 3030, 1020 (all from Johnson Matthey & Brandenberger).

A particularly suitable organoaluminate is the commercially available type K-Kat 5218 (from King Industries).

Nitrogen-containing compounds that are suitable as catalysts are in particular amines, such as, in particular N-ethyl diisopropylamine, N,N,N',N'-tetramethyl alkylenediamines, polyoxyalkylenamines, 1,4-diazabicyclo[2.2.2]octane; aminosilanes such as, in particular, 3-aminopropyl trimethoxysilane, 3-aminopropyl dimethoxymethylsilane, N-(2-aminoethyl)-3-aminopropyl trimethoxysilane, N-(2-aminoethyl)-3-aminopropyl methyldimethoxysilane, N-(2-aminoethyl)-N'-[3-(trimethoxysilyl)propyl]ethylenediamine as well as their analogs with ethoxy or isopropoxy instead of the methoxy groups on the silicon; amidines, such as, in particular, 1,8-diazabicyclo[5.4.0]undec-7-ene (DBU), 1,5-diazabicyclo[4.3.0]non-5-ene (DBN), 6-dibutylamino-1,8-diazabicyclo[5.4.0]undec-7-ene; guanidines such as, in particular, tetramethylguanidine, 2-guanidinobenzimidazole, acetylacetoneguanidine, 1,3-di-o-tolylguanidine, 2-tert.butyl-1,1,3,3-tetramethylguanidine; and imidazoles such as, in particular, N-(3-trimethoxysilylpropyl)-4,5-dihydroimidazole and N-(3-triethoxysilylpropyl)-4,5-dihydroimidazole.

Particularly suitable are also combinations of different catalysts, in particular combinations of at least one metal catalyst and at least one nitrogen-containing compound.

As catalysts, it is preferable to use organotin compounds, organotitanates, amines, amidines, guanidines and imidazoles. Organotitanates and amidines are particularly preferable.

Additional suitable components of the moisture-curing composition are, in particular, the following auxiliary substances and additives:
adhesive promoters and/or crosslinking agents, in particular silanes such as the aminosilanes already mentioned as catalyst, aminosilanes with secondary amino groups, such as, in particular, N-phenyl-, N-cyclohexyl- and N-alkylaminosilanes, moreover mercaptosilanes, epoxysilanes, (meth)acrylosilanes, anhydridosilanes, carbamatosilanes, alkylsilanes and iminosilanes, as well as oligomeric forms of these silanes, as well as adducts of primary aminosilanes with epoxysilanes or (meth)acrylosilanes or anhydridosilanes. Particularly suitable are 3-glycidoxypropyltrimethoxysilane, 3-aminopropyltrimethoxysilane, N-(2-aminoethyl)-3-aminopropyltrimethoxysilane, N-(2-aminoethyl)-N'-[3-(trimethoxysilyl)propyl]ethylenediamine, 3-mercaptopropyltrimethoxysilane, 3-ureidopropyltrimethoxysilane and the corresponding silanes with ethoxy groups instead of the methoxy groups, as well as oligomeric forms of these silanes;

plasticizers, particularly carboxylic acid esters, such as phthalates, in particular dioctyl phthalate, diisononyl phthalate or diisodecyl phthalate, adipates, in particular dioctyl adipate, azelates, sebacates, polyols, in particular polyoxyalkylene polyols or polyester polyols, glycol ethers, glycol esters, organic phosphoric and sulfonic acid esters or polybutenes;

solvents;

inorganic and organic fillers, in particular natural, ground or precipitated calcium carbonates which are optionally coated with fatty acids, in particular stearic acid, barite (heavy spar), talcs, quartz meals, quartz sand, dolomite, wollastonite, kaolin, calcined kaolins, mica (potassium-aluminum silicate), molecular sieves, aluminum oxides, aluminum hydroxides, magnesium hydroxide, silicic acids including highly dispersed silicic acids from pyrolysis processes, industrially manufactured soots, graphite, metal powders such as aluminum, copper, iron, silver or steel, PVC powders or hollow beads;

fibers, in particular glass fibers, carbon fibers, metal fibers, ceramic fibers or plastic fibers such as polyamide fibers or polyethylene fibers;

dyes;

pigments, in particular titanium dioxide or iron oxides;

drying agents, in particular tetraethoxysilane, vinyltrimethoxy- or vinyltriethoxysilane and organoalkoxysilanes which, in the α position relative to the silane group, comprise a functional group, in particular N-(methyldimethoxysilylmethyl)-O-methylcarbamate, (methacryloxymethyl)silanes, methoxymethylsilanes, orthoformic acid esters, as well as calcium oxide or molecular sieves;

rheology modifiers, in particular thickeners, in particular sheet silicates such as bentonites, derivatives of castor oil, hydrogenated castor oil, polyamides, polyurethanes, urea compounds, pyrogenic silicic acids, cellulose ethers and hydrophobically modified polyoxyethylenes;

stabilizers against oxidation, heat, light and UV radiation;

natural resins, fats or oils such as colophony, shellac, linseed oil, castor oil and soybean oil;

nonreactive polymers, such as, in particular, homopolymers or copolymers of unsaturated monomers, in particular from the group comprising ethylene, propylene, butylene, isobutylene, isoprene, vinyl acetate and alkyl (meth)acrylates, in particular polyethylenes (PE), polypropylenes (PP), polyisobutylenes, ethylene vinyl acetate copolymers (EVA) and atactic poly-α-olefins (APAO);

flame-retardant substances, in particular the already mentioned fillers, aluminum hydroxide and magnesium hydroxide, as well as, in particular, organic phosphoric acid esters such as, in particular, triethyl phosphate, tricresyl phosphate, triphenyl phosphate, diphenylcresyl phosphate, isodecyl diphenyl phosphate, tris(1,3-dichloro-2-propyl)phosphate, tris(2-chloroethyl)phosphate, tris(2-ethylhexyl)phosphate, tris(chloroisopropyl)phosphate, tris(chloropropyl) phosphate, isopropylated triphenyl phosphate, mono-, bis- and tris(isopropylphenyl)phosphates of different isopropylation degree, resorcinol-bis(diphenyl phosphate), bisphenol A bis(diphenylphosphate) and ammonium polyphosphates;

surfactants, in particular crosslinking agents, leveling agents, deaerating agents or defoaming agents;

biocides, particularly algicides, fungicides or substances that inhibit fungal growth; as well as additional substances that are usually used in moisture-curing compositions.

It can be appropriate to chemically or physically dry certain components before mixing them in the moisture-curing composition.

The moisture-curing composition can contain additional oligomers or polymers containing silane groups, in addition to the polymer with end groups of formula (I).

In a preferred embodiment, the moisture-curing composition is free of organotin compounds. This can be advantageous for ecological and/or toxicological reasons.

In an additional preferred embodiment, the moisture-curing composition does not release methanol as it cures. This can be advantageous for ecological and/or toxicological reasons.

The moisture-curing composition is preferably manufactured and stored with exclusion of moisture. Typically, the composition is storage-stable, that is to say it can be stored with exclusion of moisture in a suitable packaging or arrangement, such as, in particular, in a drum, a bag or a cartridge, for a time period from several months to one year and longer, without its application properties or its properties after the curing having changed to an extent relevant to its use. Usually, the storage stability is determined by measuring the viscosity and/or the press-out force.

The moisture-curing composition can be present in the form of a single-component or in the form of a two-component composition.

In the present document, "single-component" refers to a curable composition for which all the ingredients of the composition are stored in the same container, and which is storage-stable at room temperature for a time period from several weeks to several months and curable under the effect of moisture.

In the present document, the term "two-component" denotes a composition for which the ingredients of the composition are present in two different components which are stored in mutually separate containers and which are each individually storage-stable at room temperature. It is only shortly before or at the time of the application of the composition that the two components are mixed with one another, after which the mixed composition cures, wherein the curing occurs or is completed only due to the etffect of moisture.

During the application of the moisture-curing composition to at least one solid or article, the silane groups present come in contact with moisture. The silane groups have the property of hydrolyzing in contact with moisture. In the process, organosilanols and, due to subsequent condensation reactions, organosiloxanes form. As a result of this reaction, the composition finally cures completely. This process is also referred to as crosslinking. Moreover, silanol groups can condense with, for example, hydroxyl groups of the substrate onto which the composition is applied, as a result of which, during the curing, an excellent adhesion of the composition to the substrate can develop.

The water required for the curing can originate either from the air (air moisture) or the composition can be brought in contact with a water-containing component, for example, by brushing, for example, with a smoothing agent, or by spraying, or a water-containing component can be added to the composition at the time of the application, for example, in the form of a water-containing paste which is mixed in, for example, via a static mixer.

The curing occurs at varying speed depending on temperature, contact type, the amount of the humidity and the presence of catalysts, if any. In the case of curing by means of air moisture, a skin forms first on the surface of the composition. The so-called skin formation time accordingly represents a measure of the curing rate.

An additional subject matter of the present invention thus relates to a cured composition obtained from the curing of the moisture-curing composition under the effect of moisture.

In the cured state, the composition has resilient properties, in particular a good strength and good extensibility, a good heat resistance and good adherence properties on various substrates. As a result, it is suitable for numerous uses, in particular, as fiber composite (composite), casting composition, sealant, adhesive, covering, coating or paint in construction and industry applications, for example, as an electrical insulation composition, spackling compound, seam sealant, assembly adhesive, car body adhesive, plate adhesive, sandwich element adhesive, laminating adhesive, laminate adhesive, anchoring adhesive, bottom covering and coating, balcony and roof coating, concrete protection coating, parking garage coating as well as protective paint against corrosion, as sealant, paint, lacquer and primer.

The moisture-curing composition is particularly suitable as adhesive and/or sealant, in particular for joint sealing and for resilient adhesive compounds in construction and industry applications.

An additional subject matter of the present invention is thus the use of the moisture-curing composition as resilient adhesive and/or resilient sealant.

For use of the composition as a sealant, for example, for joining in building constructions and civil engineering, or for use as an adhesive for resilient adhesive bonding, for example, in vehicle construction, the composition preferably has a pasty consistency with sheer thinning properties. Such a pasty sealant or adhesive is applied to the substrate by means of an appropriate apparatus. Suitable application methods are, for example, application from commercial cartridges which are operated manually or by means of pressurized air, or from a drum or hobbock by means of a conveyance pump or of an extruder, optionally by means of an application robot.

A sealant or adhesive with good application properties has a high creeping strength and short thread forming. This means that after the application it remains in the applied form, that is to say it does not flow apart, and, after the application apparatus has been removed, it forms no thread or only a very short thread, so that the substrate is not soiled. An adhesive for elastic adhesive bonding, for example, in vehicle construction, is applied preferably in the form of a bead having a substantially round or triangular cross-sectional surface.

In the application as adhesive, the composition is applied to a substrate S1 and/or a substrate S2. The adhesive can thus be applied to one or the other substrate or to both substrates. Subsequently, the parts to be adhesively bonded are joined, and thereafter the adhesive cures by contact with moisture. Here one must ensure that the joining of the parts occurs within the so-called open time, in order to guarantee that the two joined parts are adhesively bonded to one another in a reliable manner.

In the application as sealant, the composition is applied between the substrates S1 and S2, and subsequently the curing of the composition occurs by contact with moisture. Usually the sealant is pressed into a joint.

In both applications, the substrate SI can be the same as or different from substrate S2.

Suitable substrates S1 or S2 are in particular
glass, glass ceramic, concrete, mortar, brick, tile, plaster and natural rock such as granite or marble;
metals and alloys, such as aluminum, iron, steel and non-ferrous metals as well as surface finished metals and alloys, such as zinc coated or chromium coated metals;
leather, textiles, paper, wood, with resins, for example, phenol, melamine or epoxide resins, bonded wood materials, resin-textile composites and other so-called polymer composites;
plastics, such as polyvinyl chloride (hard and soft PVC), acrcylonitrile-butadiene-styrene copolymers (ABS), polycarbonate (PC), polyamide (PA), polyesters, poly (methyl methacrylate) (PM MA), polyesters, epoxide resins, polyurethanes (PUR), polyoxymethylene (POM), polyolefins (PO), polyethylene (PE) or polypropylene (PP), ethylene/propylene copolymers (EPM) and ethylene/propylenediene terpolymers (EPDM), wherein the plastics can preferably be surface-treated by plasma, corona or flames;
fiber-reinforced plastics, such as carbon fiber-reinforced plastics (CFP), glass fiber reinforced plastics (GFP) and sheet molding compounds (SMC);
coated substrates, such as powder-coated metals or alloys;
paints and lacquers, in particular car top-coat lacquers.

If necessary, the substrates can be subjected to a preliminary treatment before the application of the adhesive or sealant. Such preliminary treatments include in particular physical and/or chemical cleaning processes, for example, grinding, sandblasting, brushing or the like, or treatment with cleaning agents or solvents, or the application of an adhesive promoter, an adhesive promoter solution or a primer.

After the adhesive bonding or sealing of the substrates S1 and S2 by means of a composition according to the invention, an adhesively bonded or sealed article is obtained. Such an article can be a building, in particular a structure built by building construction or civil engineering, or a transport means, for example a water or land vehicle, in particular a car, a bus, a truck, a train or a ship, or an add-on part thereof.

EXAMPLES

Embodiment examples are indicated below, which are intended to further explain the described invention. The invention is naturally not limited to these described embodiment examples.

"Standard atmospheric conditions" refers to a temperature of 23±1° C. and a relative humidity of 50±5%. "SAC" stands for "standard atmospheric conditions."

Viscosities were determined on a thermostated cone-plate viscometer Rheotec RC30 (cone diameter 50 mm, cone angle 1°, cone tip-plate distance 0.05 mm, shearing rate 10 $s^{-1}$) at a temperature of 20° C.

1. Preparation of Hydroxysilanes

Hydroxysilane HS-1: N-(3-Triethoxysilylpropyl)-4-hydroxyoctanamide

In a round-bottom flask, 20.0 g (90.4 mmol) 3-aminopropyltriethoxysilane (Dynasylan® AMEO from Evonik Degussa) and 13.2 g (93.1 mmol) γ-octalactone were stirred under a nitrogen atmosphere for approximately 8 h at 140° C., until no further reaction progress was observed by IR. The raw product was subjected to a further treatment for 30 minutes at 80° C. and approximately 2 mbar. A liquid product with a theoretical OH equivalent weight of 363.3 g was obtained.

Hydroxysilane H-2: N-(3-Triethoxysilylpropyl)-5-hydroxydecanamide 20.0 g (90.4 mmol) 3-aminopropyltriethoxysilane and 15.8 g (93.1 mmol) δ-decalactone were reacted as described for the hydroxysilane HS-1. A liquid product with a theoretical OH equivalent weight of 392.2 g was obtained.

Hydroxysilane HS-3: N-(3-Triethoxysilylpropyl)-6-hydroxydecanamide 20.0 g (90.4 mmol) 3-aminopropyltriethoxysilane and 15.8 g (93.1 mmol) ϵ-decalactone were reacted as described for the hydroxysilane HS-1. A liquid product with a theoretical OH equivalent weight of 392.2 g was obtained.

Hydroxysilane HS-4 (Comparison)N-(3-Triethoxysilylpropyl)-4-hydroxybutanamide 20.0 g (90.4 mmol) 3-aminopropyltriethoxysilane and 8.0 g (93.1 nmol) δ-butyrolactone were reacted as described for the hydroxysilane HS-1. A liquid product with a theoretical OH equivalent weight of 307.7 g was obtained.

Hydroxysilane HS-5 (Comparison): N-(3-Triethoxysilylpropyl)-5-hydroxypentanamide 20.0 g (90.4 mmol) 3-aminopropyltriethoxysilane and 9.3 g (93.1 mmol) δ-valerolactone were reacted as described for the hydroxysilane HS-1. A liquid product with a theoretical OH equivalent weight of 321.5 g was obtained.

Hydroxysilane HS-6 (Comparison): N-(3-Triethoxysilylpropyl)-6-hydroxyhexanamide 20.0 g (90.4 mmol) 3-aminopropyltriethoxysilane and 10.6 g (93.1 mmol) ϵ-caprolactone were reacted as described for the hydroxysilane HS-1. A liquid product with a theoretical OH equivalent weight of 335.6 g was obtained.

Hydroxysilane HS-7 (Comparison)

20.0 g (90.4 mmol) 3-aminopropyltriethoxysilane and 9.5 g (93.1 mmol) 1,2-propylene carbonate were reacted analogously to Example 1 in U.S. Pat. No. 5,587,502. A liquid product with a theoretical OH equivalent weight of 323.5 g was obtained.

Hydroxysilane HS-8 (Comparison)

20.0 g (90.4 mmol) 3-aminopropyltriethoxysilane and 8.2 g (93.1 mmol) ethylene carbonate were reacted analogously to Example 1 in U.S. Pat. No. 5,587,502. A liquid product with a theoretical OH equivalent weight of 309.5 g was obtained.

Hydroxysilane HS-9 (Comparison)

20.0 g (90.4 mmol) 3-aminopropyltriethoxysilane and 7.5 g (87.6 mmol) β-butyrolactone were reacted analogously to Example 1 in U.S. Pat. No. 5,587,502. A liquid product with a theoretical OH equivalent weight of 307.5 g was obtained.

Hydroxysilane HS-10 (Comparison)

20.0 g (90.4 mmol) 3-aminopropyltriethoxysilane and 7.5 g (87.6 mmol) f3-butyrolactone were reacted analogously to Example 1 in U.S. Pat. No. 5,587,502. The raw product was subjected to a further treatment for 30 minutes at 80° C. and approximately 2 mbar. A liquid product with a theoretical OH equivalent weight of 307.5 g was obtained.

Hydroxysilane HS11: N-(3-Triethoxysilylpropyl)-4-hydroxypentanamide 20.0 g (90.4 mmol) 3-aminopropyltriethoxysilane and 10.9 g (108.5 mmol) γ-valerolactone were reacted as described for the hydroxysilane HS-1. A liquid product with a theoretical OH equivalent weight of 321.5 g was obtained.

2. Preparation of Polymers Containing Silane Groups

Polymers SP-1 to -5 and SP-13 and Comparison Polymers SP-6 to SP-12

For each polymer, 100 parts by weight (PW) of the polymer containing isocyanate groups indicated in Table 1, Polymer-1, -2 or -3, were mixed with the hydroxysilane indicated in Table 1, wherein first in each case theoretically 1.10 mol hydroxysilane was used per equivalent of the polymer containing isocyanate groups. This mixture was stirred under a nitrogen atmosphere for 2 hours at 90° C., and subsequently a check by IR spectroscopy was carried out to determine whether isocyanate groups were still present in the mixture. If it was still possible to detect isocyanate groups, an additional 0.05 mol hydroxysilane per initially present equivalent of isocyanate groups was added, and after an additional 30 minutes at 90° C., a check was carried out again by IR spectroscopy to determine whether isocyanate groups could still be detected. If so, an additional 0.10 mol hydroxysilane per initially present equivalent of isocyanate groups was added, and after 30 minutes at 90° C., a check was carried out again by IR spectroscopy to determine whether isocyanate groups could still be detected. This process was repeated until isocyanate groups were no longer detected in the reaction mixture. The comparison polymers SP-11 and SP-12 were an exception to this procedure. Based on the IR spectra, after the addition of the first portion of hydroxysilane. isocyanate groups were still present, with SP-11 on the order of magnitude of 5% and with SP-12 on the order of magnitude of 30% of the originally present isocyanate groups. Nevertheless, with these two polymers, no additional hydroxysilane was added. Subsequently, the reaction mixture was cooled and stored with exclusion of moisture. The respective composition of the polymers containing silane groups is indicated in Table 1. The total number of mol hydroxysilane per equivalent of isocyanate groups is indicated in Table 1 in abbreviated form with "HO-silane/NCO."

The properties of the polymers containing silane groups obtained are indicated in Table 1.

The Polymer-1 was produced by mixing under a nitrogen atmosphere 720 g polyol Acclaim® 12200 (Bayer Material Science; low monol polyoxypropylenediol; OH number 11.0 mg KOH/g; water content approximately 0.02 wt %), 34.5 g isophorone diisocyanate (Vestanat® IPDI, Evonik Degussa), 80.0 g diisodecyl phthalate and 0.2 g dibutyltin dilaurate, heated under constant stirring at 90° C., and left at this temperature until the titrimetrically determined content of free isocyanate groups had reached a value of 0.73 wt %. The product was cooled to room temperature and stored with exclusion of moisture.

The Polymer-2 was produced by mixing under a nitrogen atmosphere 720 g polyol Acclaim® 12200 (Bayer Material Science; low monol polyoxypropylenediol; OH number 11.0 mg KOH/g; water content approximately 0.02 wt %), 26.1 g toluylene diisocyanate (Desmodur® T 80 P, Bayer), 75.4 g diisodecyl phthalate and 0.2 g dibutyltin dilaurate, heated under constant stirring at 60° C., and left at this temperature until the titrimetrically determined content of free isocyanate groups had reached a value of 0.72 wt %. The product was cooled to room temperature and stored with exclusion of moisture.

The Polymer-3 was produced by mixing under a nitrogen atmosphere 600 g polyol Acclaim® 4200 N (Bayer Material Science; low monol polyoxypropylenediol; OH number 28.1 mg KOH/g; water content approximately 0.02 wt %), 54.1 g isophorone diisocyanate (Vestanat® IPDI, Evonik Degussa), 80.0 g diisodecyl phthalate and 0.2 g dibutyltin dilaurate, heated under constant stirring at 90° C., and left at this temperature until the titrimetrically determined content of free isocyanate groups had reached a value of 1.00 wt %. The product was cooled to room temperature and stored with exclusion of moisture.

isocyanate groups were reacted by adding 2.0 g ethanol at 60° C. under a nitrogen atmosphere for 30 minutes, and the mixture was subsequently subjected to a further treatment for 30 minutes at 80° C. and approximately 2 mbar. The product was cooled to room temperature and stored with exclusion of moisture.

3. Preparation of Moisture-Curing Compositions

Compositions Z-1 to Z-5 and Comparison Compositions Z-6 to Z-9 For each composition, the ingredients indicated in Table 2 were mixed with moisture exclusion in the indicated quantities (in parts by weight) by means of a centrifugal mixer (SpeedMixer™ DAC 150, FlackTek Inc.) and stored. Each composition was checked as follows:

For the determination of the skin formation time, several grams of the composition were applied in a layer thickness of approximately 2 mm to cardboard and, under standard atmospheric conditions, the time was determined in each

TABLE 1

Composition and properties of the polymers containing silane groups according to the invention SP-1 to SP-5 and SP-13 and the comparison polymers SP-6 to SP-12. "Comp." stands for "Comparison."

| | SP-1 | SP-2 | SP-3 | SP-4 | SP-5 | SP-13 | SP-6 (Comp.) | SP-7 (Comp.) | SP-8 (Comp.) | SP-9 (Comp.) | SP-10 (Comp.) | SP-11 (Comp.) | SP-12 (Comp.) |
|---|---|---|---|---|---|---|---|---|---|---|---|---|---|
| Polymer-1 | 100.0 | 100.0 | 100.0 | — | — | 100.0 | 100.0 | 100.0 | 100.0 | 100.0 | 100.0 | 100.0 | 100.0 |
| Polymer-2 | — | — | — | 100.0 | — | — | — | — | — | — | — | — | — |
| Polymer-3 | — | — | — | — | 100.0 | — | — | — | — | — | — | — | — |
| Hydroxysilane | HS-1 | HS-2 | HS-3 | HS-1 | HS-1 | HS-11 | HS-4 | HS-5 | HS-6 | HS-7 | HS-8 | HS-9 | HS-10 |
| | 6.92 | 7.46 | 7.46 | 6.93 | 9.52 | 6.12 | 9.33 | 9.20 | 7.24 | 6.10 | 5.90 | 5.86 | 5.86 |
| HO-silane/NCO | 1.10 | 1.10 | 1.10 | 1.10 | 1.10 | 1.10 | 1.75 | 1.65 | 1.25 | 1.10 | 1.10 | 1.10* | 1.10* |
| Viscosity [Pa · s] | 99 | 98 | 135 | 82 | 98 | 129 | 185 | 131 | 112 | 52 | 69 | 71 | 51 |

*Isocyanate groups were still present

The high quantities used of the hydrosilanes HS-4, HS-5 and HS-6, which are required to prepare the comparison polymers SP-6, SP-7 and SP-8, are an indication that the OH content of these hydroxysilanes is much less than the theoretical value, which is presumably explained by a considerable content of cyclic silane compounds according to formula (VI).

For comparison purposes, the following polymers containing silane groups were prepared additionally:

Polymer SP-14 (Comparison)

To 100.0 g of the above-described Polymer-1, 7.50 g (19.1 mmol, NH/NCO=1.10) N-(3-triethoxysilylpropyl)aspartic acid diethyl ester were added. This mixture was stirred under a nitrogen atmosphere for 2 hours at 90° C., and then cooled, and stored with exclusion of humidity. No further isocyanate groups could be detected by IR spectroscopy.

Polymer SP-15 (Comparison)

200.0 g Polyol Acclaim® 12200 (Bayer Material Science; low monol polyoxypropylenediol; OH number 11.0 mg KOH/g; water content approximately 0.02 wt %), 22.2 g diisodecyl phthalate, 10.4 g isocyanatopropyltriethoxysilane and 0.2 g dibutyltin dilaurate were mixed under a nitrogen atmosphere, heated under constant stirring to 80° C., and left for 2 hours at this temperature until no further reaction progress was observed by IR spectroscopy. The remaining case until the first time that no residues remained on the pipette after slightly tapping the surface of the composition with a pipette made of LDPE.

For the determination of the mechanical properties, the composition was poured onto a PTFE-coated foil to form a film having a thickness of 2 mm, which was stored for 2 weeks under standard atmospheric conditions, several dumbbell shaped samples having a length of 75 mm, with a bar length of 30 mm and a bar width of 4 mm, were punched from the film, and these dumbbell shaped samples were tested according to DIN EN 53504 at a traction rate of 200 mm/min to determine the tensile strength (force at break), elongation at rupture and E modulus (E modulus at 0.5-50% elongation).

The Shore A hardness was determined according to DIN 53505 on test bodies cured for 14 days under standard atmospheric conditions.

These results are provided with the addition "SAC:".

As a measure of the heat resistance, several dumbbell shaped samples, or the Shore A test body, were, in addition, stored, after the 2 weeks under standard atmospheric conditions, for 1 week at 90° C. in an ambient oven, and then checked in the same manner for tensile strength, elongation at rupture and E modulus, and for the Shore A hardness. These results are provided with the addition "90° C.:".

The results are reproduced in Table 2.

TABLE 2

Composition and properties of the compositions Z-1 to Z-5 and of the comparison compositions Z-6 to Z-9. "Comp." stands for "Comparison."

| | Composition | | | | | | | | |
|---|---|---|---|---|---|---|---|---|---|
| | Z-1 | Z-2 | Z-3 | Z-4 | Z-5 | Z-6 (Comp.) | Z-7 (Comp.) | Z-8 (Comp.) | Z-9 (Comp.) |
| Polymer (type, quantity) | SP-1, 94.83 | SP-2, 94.83 | SP-3, 94.83 | SP-4, 94.83 | SP-5, 94.83 | SP-6, 94.83 | SP-7, 94.83 | SP-8, 94.83 | SP-9, 94.83 |
| Dynasylan ® AMEO [1] | 3.80 | 3.80 | 3.80 | 3.80 | 3.80 | 3.80 | 3.80 | 3.80 | 3.80 |
| Polycat ® DBU [2] | 0.34 | 0.34 | 0.34 | 0.34 | 0.34 | 0.34 | 0.34 | 0.34 | 0.34 |
| Tyzor ® IBAY [3] | 1.03 | 1.03 | 1.03 | 1.03 | 1.03 | 1.03 | 1.03 | 1.03 | 1.03 |
| Skin formation time [min] | 34 | 85 | 110 | 90 | 120 | 26 | 50 | 120 | 180 |
| SAC: Shore A | 29 | 27 | 16 | 34 | 45 | 28 | 20 | 1.2 | 42 |
| Tensile strength [MPa] | 0.57 | 0.76 | 0.40 | 0.63 | 0.90 | 0.68 | 0.67 | 0.61 | 0.75 |
| Elongation at rupture [%] | 133 | 200 | 152 | 103 | 88 | 160 | 200 | 198 | 96 |
| E modulus [MPa] | 0.49 | 0.44 | 0.22 | 0.68 | 1.06 | 0.46 | 0.26 | 0.19 | 0.89 |
| 90° C.: Shore A | 24 | 23 | 13 | 13 | 36 | 20 | 15 [5] | 9 [5] | 24 [5] |
| Tensile strength [MPa] | 0.24 | 0.30 | 0.19 | 0.24 | 0.32 | 0.28 | n.m.[4] | n.m.[4] | n.m.[4] |
| Elongation at rupture [%] | 76 | 91 | 73 | 55 | 47 | 88 | n.m.[4] | n.m.[4] | n.m.[4] |
| E modulus [MPa] | 0.25 | 0.27 | 0.17 | 0.32 | 0.51 | 0.26 | n.m.[4] | n.m.[4] | n.m.[4] |

[1] 3-Aminopropyltriethoxysilane from Evonik Degussa
[2] 1,8-Diazabicyclo[5.4.0]undec-7-ene from Air Products
[3] Titanium(IV)-bis(ethylacetoacetato) complex from Du Pont/Dorf Ketal
[4] "n.m." stands for "not measurable," the dumbbell shaped samples melted
[5] Test body with hard surface and molten core Compositions Z-10 to Z-12 and Comparison Compositions Z-13 to Z-14

For each composition, 15.00 parts by weight (PW) of the polymer containing silane groups indicated in Table 3, 20.00 PW diisodecyl phthalate, 2.00 PW thixotropic paste, 1.00 PW vinyl triethoxysilane (Dynasylan® VTEO from Evonik Degussa), 10.00 PW precipitated coated calcium carbonate (Socal® U 1 S2 from Solvay), 50.00 PW calcium carbonate (Omyacarb®5 GU from Omya), 0.75 PW 3-aminopropyl-triethoxysilane (Dynasylan® AMEO from Evonik Degussa), 0.20 PW 1,8-diazabicyclo[5.4.0]undec-7-ene (Polycat® DBU from Air Products) and 1.00 PW titanium(IV)-bis(ethylacetoacetato) complex (Tyzor® IBAY from Du Pont/Dorf Ketal) were mixed by means of a centrifugal mixer (SpeedMixer® DAC 150, FlackTek Inc.) with exclusion of moisture and stored. Each composition was tested as follows:

As measure for the storage stability, the viscosity was determined after storage with exclusion of moisture for 7 days under SAC ("Viscosity (SAC)") and a second time after the additional storage for 7 days at 60° C. ("Viscosity (60° C.)").

The skin formation time, tensile strength, elongation at rupture, E moduli and shore A hardnesses were determined in each case as for the composition Z-1. However, for the hot storage, the dumbbell shaped samples were stored, after the 2 weeks under standard atmospheric conditions, for 4 weeks at 100° C. These results are provided with the addition "100° C.:".

The results are reproduced in Table 3.

The thixotropic paste was prepared by placing in a vacuum mixer 300 g diisodecyl phthalate (Palatinol® Z, BASF) and 48 g 4,4'-methylene diphenyl diisocyanate (Desmodur® 44 MC L, Bayer) and slightly warming, followed by the slow dropwise addition under vigorous stirring of 27 g monobutylamine. The forming paste continued to be stirred for one hour under a vacuum and with cooling.

TABLE 3

Composition and properties of the compositions according to the invention Z-10 to Z-12 and the comparison compositions Z-13 to Z-14.

| | Composition | | | | |
|---|---|---|---|---|---|
| | Z-10 | Z-11 | Z-12 | Z-13 (Comp.) | Z-14 (Comp.) |
| Polymer | SP-1 | SP-2 | SP-4 | SP-6 | SP-7 |
| Viscosity (SAC) [Pa · s] | 66 | 52 | 26 | 62 | 59 |
| Viscosity (60° C.) [Pa · s] | 90 | 74 | 29 | 71 | 64 |
| Skin formation time [min] | 45 | 85 | 85 | 40 | 75 |
| SAC: Shore A | 26 | 21 | 28 | 25 | 18 |
| Tensile strength [MPa] | 0.96 | 0.70 | 0.79 | 0.82 | 0.65 |
| Elongation at rupture [%] | 570 | 475 | 437 | 315 | 240 |
| E modulus [MPa] | 0.55 | 0.43 | 68 | 0.57 | 0.44 |
| 100° C.: Shore A | 21 | 17 | 18 | n.m.[1] | n.m.[1] |
| Tensile strength [MPa] | 0.21 | 0.28 | 0.39 | n.m.[1] | n.m.[1] |
| Elongation at rupture [%] | 85 | 100 | 71 | n.m.[1] | n.m.[1] |
| E modulus [MPa] | 0.24 | 0.28 | 0.58 | n.m.[1] | n.m.[1] |

[1] "n.m." stands for "not measurable," the test samples melted
"Comp." stands for "Comparison"

Compositions Z-15 and Z-16 and Comparison Compositions Z-17 to Z-30

For each composition, the ingredients indicated in Tables 4 and 5 were mixed with exclusion of moisture in the indicated quantities (in parts by weight) by means of a centrifugal mixer (SpeedMixer™ DAC 150, FlackTek Inc.) and stored. Each composition was tested as described for the composition Z-10.

The results are indicated in Tables 4 and 5.

From Tables 4 and 5 one can see in particular that, with the polymers containing silane groups according to the invention, compositions can be obtained that have a rapid skin formation time and excellent heat resistance.

TABLE 4

Composition and properties of the composition according to the invention Z-15
and the Comparison Compositions Z-17 to Z-23. "Comp." stands for "Comparison"

| | Composition | | | | | | | |
|---|---|---|---|---|---|---|---|---|
| | Z-15 | Z-17 (Comp.) | Z-18 (Comp.) | Z-19 (Comp.) | Z-20 (Comp.) | Z-21 (Comp.) | Z-22 (Comp.) | Z-23 (Comp.) |
| Polymer | SP-13, 15.00 | SP-10, 15.00 | SP-9, 15.00 | SP-6, 15.00 | SP-11, 15.00 | SP-12, 15.00 | SP-14, 15.00 | SP-15, 15.00 |
| Diisodecyl phthalate | 20.00 | 20.00 | 20.00 | 20.00 | 20.00 | 20.00 | 20.00 | 20.00 |
| Thixotropic paste | 2.00 | 2.00 | 2.00 | 2.00 | 2.00 | 2.00 | 2.00 | 2.00 |
| Vinyl triethoxysilane | 1.00 | 1.00 | 1.00 | 1.00 | 1.00 | 1.00 | 1.00 | 1.00 |
| Socal ® U 1 S2 | 10.00 | 10.00 | 10.00 | 10.00 | 10.00 | 10.00 | 10.00 | 10.00 |
| Omyacarb ® 5 GU | 50.00 | 50.00 | 50.00 | 50.00 | 50.00 | 50.00 | 50.00 | 50.00 |
| Geniosil ® GF-94 [1] | 0.75 | 0.75 | 0.75 | 0.75 | 0.75 | 0.75 | 0.75 | 0.75 |
| Polycat ® DBU | 0.10 | 0.10 | 0.10 | 0.10 | 0.10 | 0.10 | 0.10 | 0.10 |
| Tyzor ® IBAY | 1.25 | 1.25 | 1.25 | 1.25 | 1.25 | 1.25 | 1.25 | 1.25 |
| Skin formation time [min] | 40 | 45 | 95 | 45 | 35 | 20 | 100 | 90 |
| SAC: Shore A | 36 | 26 | 27 | 22 | 35 | 34 | 30 | 37 |
| Tensile strength [MPa] | 1.10 | 0.90 | 1.05 | 0.98 | 1.04 | 1.06 | 0.89 | 0.98 |
| Elongation at rupture [%] | 250 | 120 | 145 | 125 | 135 | 185 | 155 | 120 |
| E modulus [MPa] | 1.01 | 0.75 | 0.88 | 0.85 | 0.90 | 0.93 | 0.77 | 1.21 |
| 100° C.: Shore A | 36 | 15 | 21 | 17 | 14 | 15 | 27 | 40 |
| Tensile strength [MPa] | 0.73 | n.m.[2] | 0.71 | n.m.[2] | n.m.[2] | n.m.[2] | 0.31 | n.m.[2] |
| Elongation at rupture [%] | 110 | n.m.[2] | 105 | n.m.[2] | n.m.[2] | n.m.[2] | 25 | n.m.[2] |
| E modulus [MPa] | 0.77 | n.m.[2] | 0.66 | n.m.[2] | n.m.[2] | n.m.[2] | — | n.m.[2] |

[1] N-(2-Aminoethyl)-3-aminopropyltriethoxysilane from Wacker
[2] "n.m." stands for "not measurable," the test bodies melted

TABLE 5

Composition and properties of the composition according to the invention Z-16
and the Comparison Compositions Z-24 to Z-30. "Comp." stands for "Comparison"

| | Composition | | | | | | | |
|---|---|---|---|---|---|---|---|---|
| | Z-16 | Z-24 (Comp.) | Z-25 (Comp.) | Z-26 (Comp.) | Z-27 (Comp.) | Z-28 (Comp.) | Z-29 (Comp.) | Z-30 (Comp.) |
| Polymer | SP-13, 15.00 | SP-10, 15.00 | SP-9, 15.00 | SP-6, 15.00 | SP-11, 15.00 | SP-12, 15.00 | SP-14, 15.00 | SP-15, 15.00 |
| Diisodecyl phthalate | 20.00 | 20.00 | 20.00 | 20.00 | 20.00 | 20.00 | 20.00 | 20.00 |
| Thixotropic paste | 2.00 | 2.00 | 2.00 | 2.00 | 2.00 | 2.00 | 2.00 | 2.00 |
| Vinyl triethoxysilane | 1.00 | 1.00 | 1.00 | 1.00 | 1.00 | 1.00 | 1.00 | 1.00 |
| Socal ® U 1 S2 | 10.00 | 10.00 | 10.00 | 10.00 | 10.00 | 10.00 | 10.00 | 10.00 |
| Omyacarb ® 5 GU | 50.00 | 50.00 | 50.00 | 50.00 | 50.00 | 50.00 | 50.00 | 50.00 |
| Tyzor ® IBAY | 1.25 | 1.25 | 1.25 | 1.25 | 1.25 | 1.25 | 1.25 | 1.25 |
| Skin formation time [min] | 50 | 70 | 75 | 50 | 80 | >300 | >300 | 95 |
| SAC: Shore A | 36 | 30 | 35 | 34 | 10 | n.m.[1] | 27 | 36 |
| Tensile strength [MPa] | 1.15 | 1.13 | 1.36 | 1.13 | 0.30 | n.m.[1] | 0.46 | 1.35 |
| Elongation at rupture [%] | 160 | 135 | 160 | 125 | 105 | n.m.[1] | 95 | 115 |
| E modulus [MPa] | 0.91 | 0.81 | 0.98 | 0.88 | 0.30 | n.m.[1] | 0.41 | 1.23 |
| 100° C.: Shore A | 33 | 19 | 20 | 16 | n.m.[2] | n.m.[1] | 25 | 43 |
| Tensile strength [MPa] | 0.87 | 0.59 | 0.72 | 0.61 | 0.11 | n.m.[1] | 0.76 | 1.08 |
| Elongation at rupture [%] | 125 | 105 | 115 | 100 | 40 | n.m.[1] | 110 | 115 |
| E modulus [MPa] | 0.69 | 0.53 | 0.63 | 0.58 | — | n.m.[1] | 0.65 | 0.95 |

[1] "n.m." stands for "not measurable," the composition remained liquid
[2] "n.m." stands for "not measurable," the test bodies melted

The invention claimed is:
1. Method for producing a polymer with end groups of formula (I), which is free of isocyanate groups,

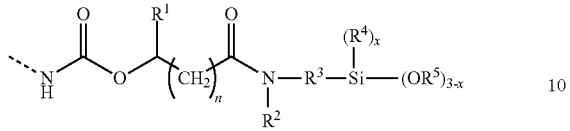

where:
R¹ stands for an alkyl group having 1 to 12 C atoms,
R² stands for a hydrogen atom or for an alkyl group having 1 to 12 C atoms, which optionally comprises ether oxygen or amine nitrogen,
R³ stands for a linear or a branched alkylene or cycloalkylene residue having 1 to 12 C atoms, optionally with aromatic parts, and optionally with one or more heteroatoms,
R⁴ stands for an alkyl group having 1 to 6 C atoms,
R⁵ stands for an alkyl group having 1 to 10 C atoms, which optionally comprises one or more ether oxygens,
n stands for 2 or 3 or 4 , and
x stands for 0 or 1,
wherein at least one hydrosilane of formula (II) is reacted with at least one polyurethane polymer containing isocyanate groups,

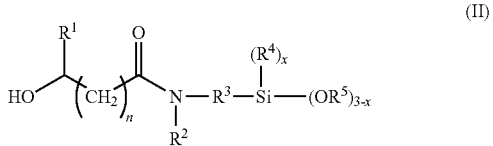

where:
R¹ stands for an alkyl group having 1 to 12 C atoms,
R² stands for a hydrogen atom or for an alkyl group having 1 to 12 C atoms, which optionally comprises ether oxygen or amine nitrogen,
R³ stands for a linear or a branched alkylene or cycloalkylene residue having 1 to 20 C atoms, optionally with aromatic parts, and optionally with one or more heteroatoms,
R⁴ stands for an alkyl group having 1 to 6 C atoms,
R⁵ stands for an alkyl group having 1 to 10 C atoms, which optionally comprises one or more ether oxygens,
n stands for 2 or 3 or 4, and
x stands for 0 or 1.

2. Method according to claim 1, wherein the residue R¹ in formula (I) stands for a residue R¹ᵃ, where R¹ᵃ stands for n-butyl, n-pentyl, n-hexyl, n-heptyl or n-octyl.

3. Method according to claim 1, wherein the residue R³ in formula (I) is selected from the group consisting of 1,3-propylene, 2-methyl-1,3-propylene, 1,4-butylene, 3-methyl-1,4-butylene and 3,3-dimethyl-1,4-butylene.

4. Method according to claim 1, wherein x in formula (I) stands for 0.

5. Method according to claim 1, wherein the polymer with end groups of formula (I) has a molecular weight in the range from 1000 to 30,000 g/mol.

6. Method according to claim 1, wherein the polymer with end groups of formula (I) comprises polyoxyalkylene units.

7. Method according to claim 1, wherein the end groups of formula (I) are bound to cycloaliphatic residues.

8. Method according to claim 1, wherein the polymer with end groups of formula (I) has 1 to 4 end groups of formula (I).

* * * * *